(12) United States Patent
Xie et al.

(10) Patent No.: US 6,726,325 B2
(45) Date of Patent: Apr. 27, 2004

(54) TRACKING ASSISTED OPTICAL COHERENCE TOMOGRAPHY

(75) Inventors: Jing-Gang Xie, Pleasanton, CA (US); Jay Wei, Fremont, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 93 days.

(21) Appl. No.: 10/086,092

(22) Filed: Feb. 26, 2002

(65) Prior Publication Data

US 2003/0160942 A1 Aug. 28, 2003

(51) Int. Cl.⁷ .................................................. A61B 3/14
(52) U.S. Cl. ...................................................... 351/209
(58) Field of Search ................................ 351/205, 208, 351/209, 210, 214, 221; 382/103, 128, 131

(56) References Cited

U.S. PATENT DOCUMENTS

| | | | |
|---|---|---|---|
| 5,321,501 A | 6/1994 | Swanson et al. | 356/345 |
| 5,459,570 A | 10/1995 | Swanson et al. | 356/345 |
| 5,506,634 A | 4/1996 | Wei et al. | 351/221 |
| 5,644,642 A | 7/1997 | Kirschbaum | 382/103 |
| 5,767,941 A | 6/1998 | Ferguson | 351/206 |
| 6,325,512 B1 | 12/2001 | Wei | 351/209 |

OTHER PUBLICATIONS

"400–Hz mechanical scanning optical delay line" by K. F. Kwong et al., *Optics Letters*, vol. 18, No. 7, Apr. 1, 1993, pp. 558–560.

"High–speed phase– and group–delay scanning with a grating–based phase control delay line" by G. J. Tearney et al., *Optics Letters*, vol. 22, No. 23, Dec. 1, 1997, pp. 1811–1813.

*Primary Examiner*—George Manuel
(74) *Attorney, Agent, or Firm*—Michael B. Einschlag

(57) ABSTRACT

One embodiment of the present invention is an optical coherence tomography ("OCT") application apparatus that performs an OCT application on an object. The OCT application apparatus includes: (a) an OCT scanning apparatus which outputs a scanning beam of OCT scanning radiation; and (b) an active tracking system that generates and projects a tracking beam of tracking radiation onto a region including a reference tracking feature; wherein the active tracking system further includes an analysis system that analyzes tracking radiation reflected from the region to detect movement of the object and to generate tracking signals, and applies the tracking signals (i) to direct the active tracking system to move the tracking beam to follow the movement of the object, and (b) as input to the OCT scanning apparatus, to direct the OCT scanning apparatus to move the scanning beam to follow the movement of the object.

20 Claims, 3 Drawing Sheets

TRACKING ASSISTED OPTICAL COHERENCE TOMOGRAPHY

TECHNICAL FIELD OF THE INVENTION

One or more embodiments of the present invention pertain to method and apparatus for performing an optical coherence tomographic examination of tissue such as an eye. In particular, the present invention relates to method and apparatus for performing an optical coherence tomographic examination of an eye using an active tracking system to lock an optical coherence tomography ("OCT") scanning beam on desired features in retinal tissue for use, for example, in imaging retinal tissue, measuring retinal and retinal nerve fiber layer thickness, mapping the topography of the optic nerve head, and so forth.

BACKGROUND OF THE INVENTION

As is well known, an optical coherence tomography ("OCT") apparatus (for example, as disclosed in U.S. Pat. No. 5,321,501 ("the '501 patent") is an optical imaging apparatus that can perform micron-resolution, cross-sectional imaging (also referred to as tomographic imaging) of biological tissue. As is also well known, to make measurements along an axial direction (i.e., into the biological tissue): (a) radiation is directed to, and reflected by, a reference mirror located in one arm (a reference arm) of a Michelson interferometer (the position of the reference mirror is scanned); and (b) in a second arm (a sample arm) of the Michelson interferometer, radiation is directed to, and scattered by, the biological tissue. Whenever the optical path difference of radiation in the two arms of the Michelson interferometer equals, or is less than, the optical coherence length of the radiation transmitted into the interferometer from a source, an optical interference signal can be detected. As disclosed in the '501 patent, a cross-sectional image of the tissue is formed by combining data from serial axial scans.

The length of time it takes to produce a tomographic image is limited by several factors: (a) the scan speed of the reference mirror in the reference arm used to obtain measurements in the axial direction; (b) the transverse scan speed of deflectors used to acquire serial axial scans; (c) signal-to-noise limits related to image quality; and (d) the speed of electronics, and any associated computer, in sampling analog OCT signals and transforming them into a pseudo color, or gray scale, image. However, in general, as the scan speed of the reference mirror goes up, the signal-to-noise ratio goes down; thereby adversely affecting the image quality. On the other hand, when imaging tissue in an eye, one is constrained to obtain images rapidly to avoid problems caused by eye movement.

At present, the scan speed of the reference mirror is a limiting factor in OCT image acquisition. To understand this, refer to U.S. Pat. No. 5,459,570 ("the '570 patent") where the reference mirror is moved by a PZT actuator. Although the scan speed of a PZT actuator can be as high as several KHz, the scan range is limited to the micron range, which micron range is not practical for in vivo human eye diagnosis where a scan range of a couple of millimeters is required for clinical use. Although the required several millimeter scan range can be obtained by mounting a retro-reflector on one end of an arm that is scanned by a galvanometer, the scan speed is limited to about a couple hundred hertz (this scan method is currently employed in a commercially available OCT scanner device made by Zeiss Humphrey Systems of Dublin Calif.).

A scan device in an OCT system that provides a two to four KHz scan speed with a useful scan range was disclosed in an article entitled "High-speed phase-and group-delay scanning with a grating-based phase control delay line" by G. J. Tearney et al. in *Optics Letters*, Vol. 22, No. 23, Dec. 1, 1997, pp. 1811–1813, which scan device was based on a phase ramping delay line principle disclosed in an article entitled "400-Hz mechanical scanning optical delay line" by K. F. Kwong et al. in *Optics Letters*, Vol. 18, No. 7, Apr. 1, 1993, pp. 558–560. A disadvantage of the scan device disclosed in the G. J. Tearney et al. article is that it is easily worn out, and there is an upper limit light power allowed for safe use in in-vivo human eye diagnosis. However, as pointed out above, with increasing scan speed, the signal-to-noise ratio will be reduced, and image quality will deteriorate.

Although OCT scan data can be used to provide tomographic images of tissue such as an eye, the OCT data obtained has many uses other than in providing an image. For example, applications of OCT data include measuring retinal and retinal nerve fiber layer thickness, mapping the topography of the optic nerve head, and so forth. However, in these applications, similar problems arise, i.e., how to obtain data having acceptable signal-to-noise ratios while taking into account movement of the tissue. In light of the above, there is a need for a method and apparatus that can obtain high quality OCT data, for example, to form tomographic scan images, while taking into account the issue of, for example, patient movement.

SUMMARY OF THE INVENTION

One or more embodiments of the present invention advantageously satisfy one or more of the above-identified needs in the art, and provide method and apparatus for performing optical coherence tomography ("OCT") applications. Specifically, one embodiment of the present invention is an OCT application apparatus that performs an OCT application on an object, which OCT application apparatus comprises: (a) an OCT scanning apparatus which outputs a scanning beam of OCT scanning radiation; and (b) an active tracking system that generates and projects a tracking beam of tracking radiation onto a region including a reference tracking feature; wherein the active tracking system further comprises an analysis system that analyzes tracking radiation reflected from the region to detect movement of the object and to generate tracking signals, and applies the tracking signals (i) to direct the active tracking system to move the tracking beam to follow the movement of the object, and (b) as input to the OCT scanning apparatus, to direct the OCT scanning apparatus to move the scanning beam to follow the movement of the object.

DETAILED DESCRIPTION

In accordance with one embodiment of the present invention, a high resolution, tomographic image of features of, for example, a human eye is obtained by performing a relatively slow optical coherence tomography ("OCT") scan. For example, some patients can keep an eye open for as long as ten (10) seconds. Advantageously, in accordance with this embodiment of the present invention, the signal-to-noise ratio of images generated by performing such a slow scan is higher that that obtained using relatively a rapid scan characteristic of the prior art since the signal-to-noise ratio of the OCT image increases with the inverse square root of the speed of the scan.

To perform a relatively slow scan in accordance with one embodiment of the present invention, a beam of OCT scanning radiation is locked onto a reference tracking feature to avoid artifacts that might occur due to patient eye movement. In accordance with this embodiment of the present invention, the OCT scan beam is locked onto the reference tracking feature by an active tracking system, which active tracking system utilizes a reflectance characteristic of the reference tracking feature to provide a tracking signal. Advantageously, such an active tracking system can operate at rates which are required for in-vivo human eye tracking rates, i.e., at rates as high as several KHz.

Although an embodiment of the present invention is described with reference to providing an OCT tomographic image, those of ordinary skill in the art will readily appreciate that embodiments of the present invention are not limited to those wherein an OCT tomographic image is produced. In particular, it is within the scope of the present invention to include embodiments wherein OCT data is obtained for uses other than and/or in conjunction with an image such as, for example and without limitation, measuring retinal and retinal nerve fiber layer thickness, mapping the topography of the optic nerve head, and so forth. Thus, an apparatus to perform any of these applications will be referred to herein as an OCT application apparatus, and a method to perform any of these applications will be referred to herein as an OCT application method.

Figure 1:
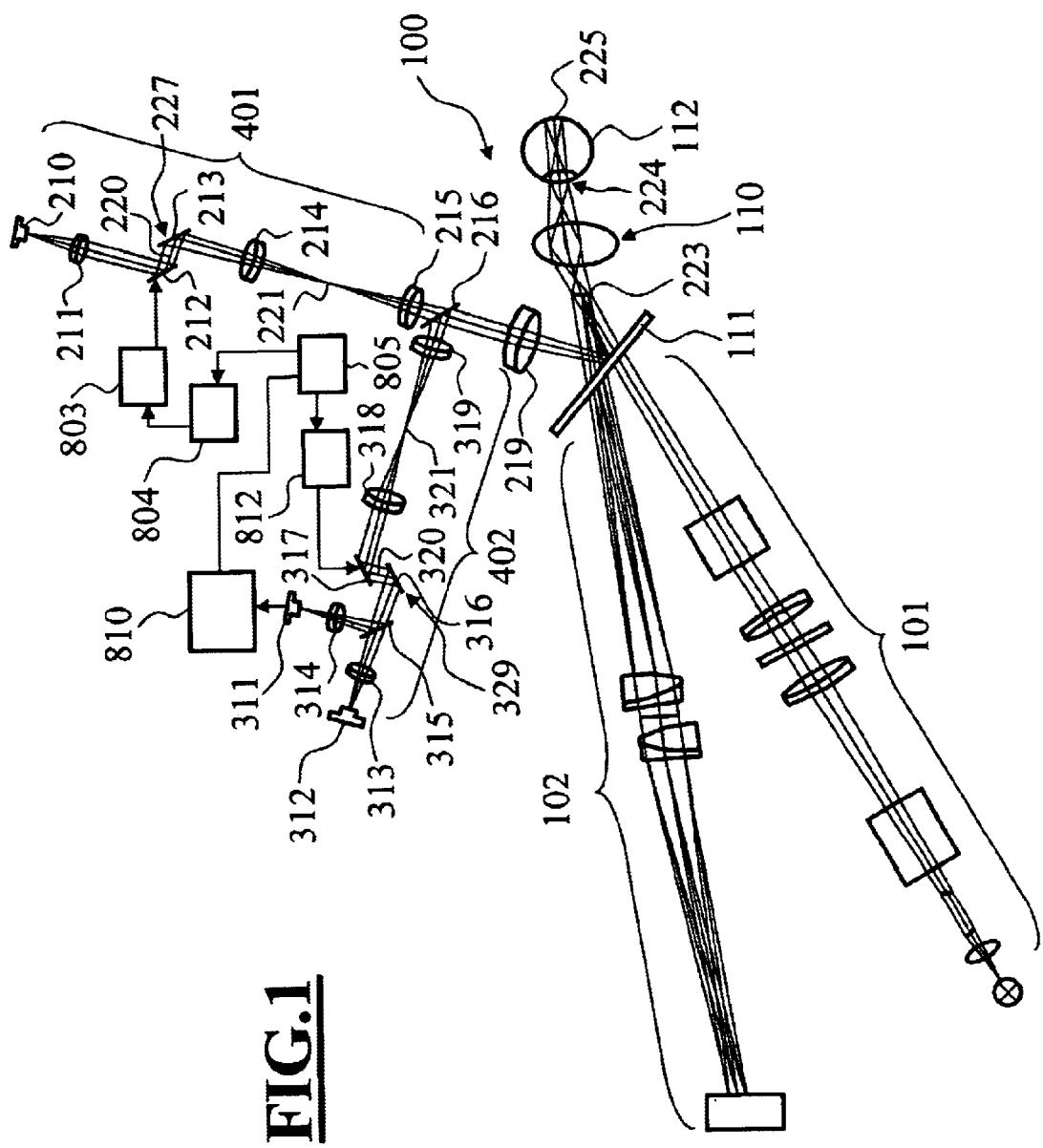
FIG. 1 shows a diagram of a portion of an embodiment of the present invention, and various optical paths associated therewith.

FIG. 1 shows a diagram of a portion of embodiment 100 of the present invention, and various optical paths associated therewith. As shown in FIG. 1, embodiment 100 comprises fundus illumination apparatus 101, viewing apparatus 102, active tracking system 402, and OCT scanning arm 401 of an OCT apparatus (in particular, OCT scanning arm 401 comprises a sample arm of an OCT scanning apparatus). The rest of the OCT apparatus (not shown) is fabricated in accordance with any one of a number of methods that are well known to those of ordinary skill in the art, and is not shown to make it easier to understand the present invention.

An embodiment of fundus illumination apparatus 101 and an embodiment of viewing apparatus 102 are disclosed in U.S. Pat. No. 5,506,634, which patent is assigned to the assignee of the present application, and which patent is incorporated herein by reference. As seen in FIG. 1, the optical path of fundus illumination apparatus 101 and the optical path of viewing apparatus 102 are combined by beamsplitter 111, and aerial image plane 223 is relayed onto the retina of eye 112 by ocular lens system 110 (as is well known to those of ordinary skill in the art, ocular lens system 110 may comprise one or more lenses) and the lens of eye 112.

FIG. 1 further shows: (a) an optical path of a beam of tracking radiation (a "tracking beam") output from active tracking system 402, and (b) an optical path of a beam of OCT scanning radiation (a "scanning beam") output from OCT scanning arm 401. As shown in FIG. 1, the scanning beam output from a face end of, for example, fiber interferometer 210, passes through collimating lens system 211 (as is well known to those of ordinary skill in the art, lens system 211 may comprise one or more lenses), and impinges upon scanning mechanism 227. As is well known to those of ordinary skill in the art, OCT scanning radiation is typically output from a short coherence length source such as, for example, a superluminescent diode. As further shown in FIG. 1, scanning mechanism 227 comprises a pair of scanning mirrors 212 and 213 that are driven, for example, and without limitation, by scan driver 803 which is driven, in turn, by signals output from control module 804. In accordance with one such embodiment, scanning mirrors 212 and 213 are reflectors that are orthogonally mounted on, for example, a pair of X-Y galvanometers, in accordance with any one of a number of methods that are well known to those of ordinary skill in the art.

As is well known to those of ordinary skill in the art, scanning mirrors pair 212 and 213 is used to generate a desired scan pattern on retina 225 to form an OCT image. A typical OCT scan pattern in a direction perpendicular to an axial scan direction is a line or a circle. In such a case, in accordance with this embodiment of the present invention, scanning mirrors pair 212 and 213 is activated to produce a scan pattern which is a line or a circle.

In accordance with this embodiment of the present invention, scanning pivot point 220 of scanning mirrors pair 212 and 213 (i.e., a middle point between scanning mirrors pair 212 and 213) is optically conjugated to pupil 224 of eye 112 by (a) one-to-one magnification, relay lens system pair 214 and 215; and (b) lens system 219 and ocular lens system 110. Thus, as was described in U.S. Pat. No. 5,506,634, there will be no vignetting in the OCT scanning beam. As is well known to those of ordinary skill in the art, lens systems 214, 215, and 219 may each comprise one or more lenses.

As shown in FIG. 1, an embodiment of active tracking system 402 comprises tracking beam radiation source 312 which is, for example and without limitation, a laser or a light emitting diode ("LED"), or any one of a number of other coherent or incoherent sources of radiation. The tracking beam output from tracking beam radiation source 312 is collimated by collimating lens system 313 (as is well known to those of ordinary skill in the art, lens system 313 may comprise one or more lenses). The collimated tracking beam passes through beamsplitter 315, and impinges upon dither mechanism 329. As further shown in FIG. 1, dither mechanism 329 comprises a pair of dithering mirrors 316 and 317 that are driven, for example, and without limitation, by dither driver 812 which is driven, in turn, by signals output from control module 805. In accordance with one such embodiment, dithering mirrors 316 and 317 are reflectors that are orthogonally mounted on, for example, a pair of X-Y galvanometers in accordance with any one of a number of methods that are well known to those of ordinary skill in the art (galvanometers with low armature inertia can be used to achieve a high-speed tracking response).

In accordance with this embodiment of the present invention, dithering pivot point 320 of dithering mirrors pair 316 and 317 (i.e., a middle point between dithering mirrors pair 316 and 317) is optically conjugated to pupil 224 of eye 112 by (a) one-to-one magnification, relay lens system pair 318 and 319; and (b) lens system 219 and ocular lens system 110. Thus, as was described in U.S. Pat. No. 5,506,634, there will be no vignetting in the tracking beam. As is well known to those of ordinary skill in the art, lens systems 318 and 319 may each comprise one or more lenses.

In accordance with this embodiment of the present invention: (a) the collimated scanning beam output from scanning mirrors pair 212 and 213 is focused by lens system 214 to point 221; (b) point 221 is optically conjugated to aerial image plane 223 through relay lens system pair 215 and 219; and (c) aerial image plane 223 is optically conjugated to retina 225 of eye 112 through ocular lens system 110 and the lens of eye 112. In addition, in accordance with this embodiment of the present invention: (a) the collimated tracking beam output from dithering mirrors pair 316 and 317 is focused by lens system 318 to point 321; (b) point 321 is optically conjugated to aerial image plane 223 through relay lens system pair 319 and 219; and (c) aerial image plane 223 is optically conjugated to retina 225 of eye 112 through ocular lens system 110 and the lens of eye 112.

As one of ordinary skill in the art will readily appreciate, the tracking beam impinges upon retina 225, and retina 225 retro-reflects at least a portion of the tracking beam. The retro-reflected tracking beam is directed (through the same optical path that brought the tracking beam to eye 112 in the first place) to beamsplitter 315. Beamsplitter 315 directs at least a portion of the retro-reflected tracking beam to impinge upon lens system lens 314 (as is well known to those of ordinary skill in the art, lens system 314 may comprise one or more lenses), and lens system 314 focuses the retro-reflected tracking beam upon photodetector 311 (for example and without limitation, a photodiode).

In accordance with this embodiment of the present invention, motion of eye 112 is detected by sensing changes in reflectance (at the wavelengths of the tracking radiation) between a reference tracking feature, and its surrounding or adjacent area. The reference tracking feature may be associated with an eye, or it may be a retro-reflecting material. However, many retinal features have a high enough reflectivity contrast with respect to the background area to be suitable for use as reference tracking features. For example, a reference tracking feature comprising an intersection of two blood vessels in the retina presents a relatively dark area when compared to surrounding retinal tissues. As another example, a reference tracking feature comprising the optical nerve head presents a relatively bright disk when compared to surrounding retinal tissues.

In accordance with this embodiment of the present invention, active tracking system 402 projects the tracking beam onto a reference tracking feature on the retina. Then, as eye 112 moves, due to reflectance differences between the reference tracking feature and the surrounding area, the intensity of the retro-reflected tracking beam detected by photodetector 311 will change. Further, in accordance with this embodiment of the present invention, the direction of motion is detected by detecting changes in reflected radiation intensity, and a tracking signal is generated to drive scanning mirrors pair 212 and 213 and dithering mirrors pair 316 and 317 to track the motion of eye 112.

In accordance with one embodiment of the present invention, a mechanism for sensing the direction of motion of eye 112 is fabricated improving upon a disclosure in U.S. Pat. No. 5,767,941 ("the '941 patent"), which '941 patent is incorporated by reference herein. In accordance with one embodiment of the present invention, active tracking system 402 locks onto a reference tracking feature by inducing small, periodic, transverse oscillations or dithers in the tracking beam. The tracking beam radiation may comprise any wavelength of radiation that can be used to detect changes in reflectance between the reference tracking feature and the surrounding area. In particular, the tracking beam may be formed using radiation output from a light emitting diode, or from any one of a number of other incoherent or coherent sources of radiation. Typically, the reference tracking feature is locked onto by the tracking beam in two dimensions with a circular dither.

As shown in FIG. 1, active tracking system 402 includes a reflectometer (beamsplitter 315, lens system 314, and photodetector 311) positioned in an optical path of the retro-reflected tracking beam to provide a reflectometer output signal having a phase corresponding to the phase of the retro-reflected tracking beam. Whenever the tracking beam traverses a region of changing reflectance, a corresponding variation in intensity of the reflectometer output signal occurs. The reflectometer output signal varies synchronously (when appropriately corrected for phase shifts) with the oscillatory motion caused by dither mechanism 329.

As shown in FIG. 1, active tracking system 402 includes signal conditioning module 810. The signal output from photodetector 311 is applied as input to signal conditioning module 810. In accordance with one embodiment of the present invention, signal conditioning module comprises conventional electronics that conditions the signal for further processing in accordance with any one of a number of methods that are well known to those of ordinary skill in the art, for example, by amplification. The conditioned signal is then applied as input to control module 805. In response, control module 805 generates: (a) tracking signals (the tracking signals are applied as input to control module 804); and (b) dither drive signals (the dither drive signals are applied as input to dither driver 812). In response to the dither drive signals, dither driver 812 causes dither mechanism 329 to: (a) dither the tracking beam in a first and a second direction with, for example, an oscillatory motion having a first phase and a second phase respectively (the first and second phases of oscillatory motion may be orthogonal to each other); and (b) track the motion of eye 112 (i.e., to control the position of the tracking beam relative to the reference tracking feature). In accordance with this embodiment of the present invention, dither mechanism 329 produces a circular dither at the reference feature whenever the oscillatory motions in the first and second directions have identical amplitudes, and have a phase difference of 90 degrees.

In addition, in response to the tracking signals applied as input from control module 805, control module 804 generates scanning drive signals that are applied as input to scan driver 803. In response to the scanning drive signals, scan driver 803 causes scanning mechanism 227 to: (a) control the position of the OCT scanning beam in accordance with predetermined scanning algorithms; and (b) track the motion of eye 112 (i.e., to control the position of the scanning beam relative to the reference tracking feature).

As will be described below in conjunction with FIG. 2, control module 805: (a) compares the phase of the conditioned reflectometer output signal with the phases of signals that caused the dither motion, and (b) generates first and second direction control signals that are coupled to dither driver 812. In response to the first and second direction control signals, dither driver 812 causes dithering mechanism 329 to react so that the tracking beam tracks relative to the reference tracking feature. As described in the '941 patent, the phase comparison produces first and second phase comparison signals that comprise DC offset voltages that are proportional to the amplitude of the components of the reflectometer signal which are in phase with the dither signals. These DC offset voltages are vector correction or error voltages that are proportional to the displacement from equilibrium per dither cycle.

As set forth in the '941 patent, a tracking velocity of the corrections is proportional to the product of a dither frequency of the dither drivers of the dither mechanism and a spatial dimension of the reference tracking feature. The useful dither frequency depends upon several factors. For example, if the beam of tracking radiation is imaged on the retina of an eye at unit magnification, a 2 KHz dither frequency will correspond to approximately a 50μ displacement per dither cycle at a target velocity of 10 cm/sec (i.e., greater than 300 degrees/sec in an eye). Such a dither frequency is sufficient to track a beam of OCT scanning radiation with a spot size of approximately 400μ.

Figure 2:
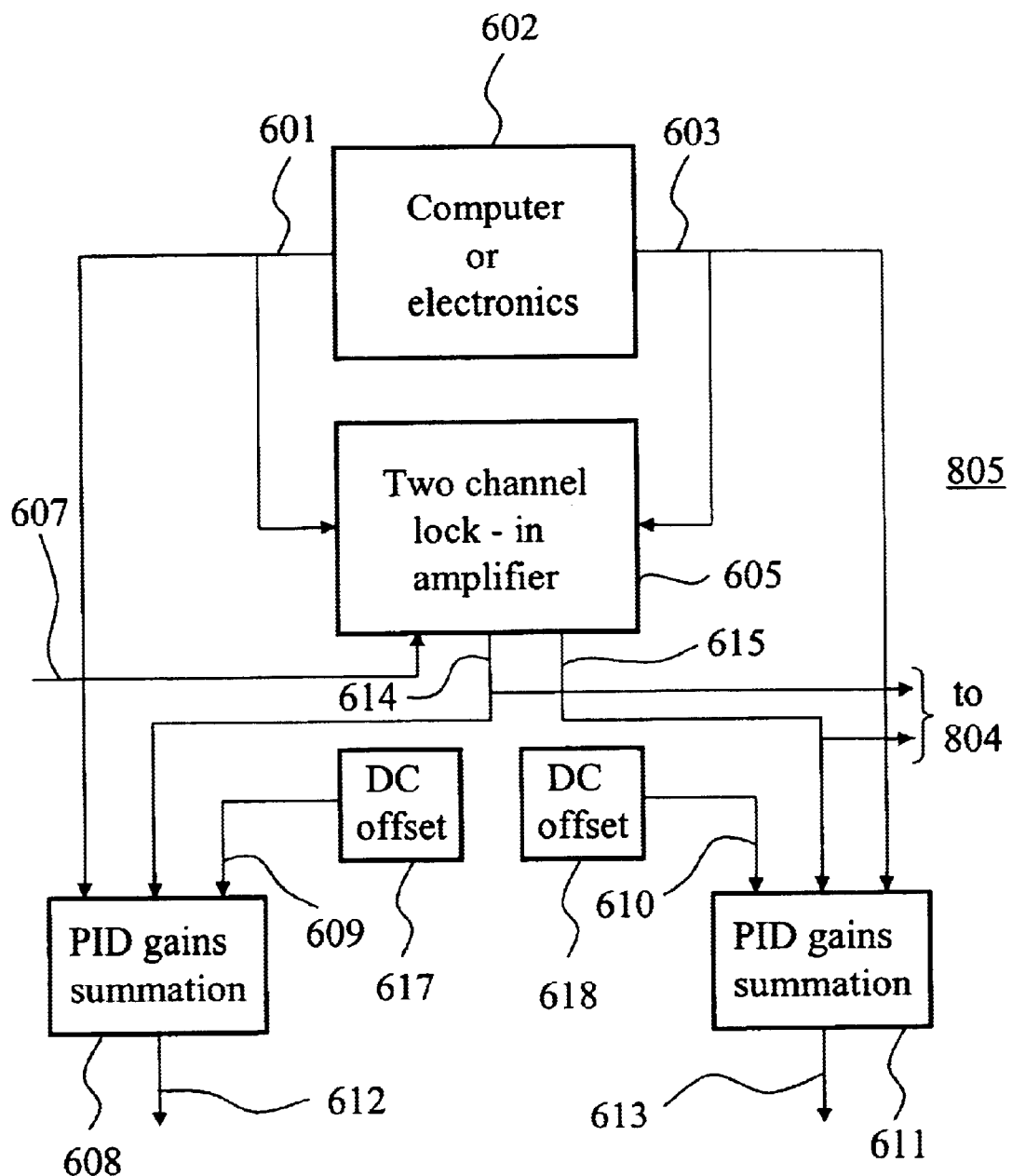
FIG. 2 is a functional block diagram of control module 805 that is fabricated in accordance with one embodiment of the present invention for use in the embodiment shown in FIG. 1.

FIG. 2 is a functional block diagram of control module 805 that is fabricated in accordance with one embodiment of the present invention. As shown in FIG. 2, computer 602 (or conventional electronics circuit 602) generates synchronized cosine signal 601 (i.e., $\cos(\omega t)$) and sine signal 603 (i.e., $\sin(\omega t)$) having circular frequency ω in accordance with any one of a number of methods that are well known to those of ordinary skill in the art. Cosine signal 601 is applied as input to dual channel, lock-in amplifier 605 (one could also use a pair of lock-in amplifiers) as an X-reference signal, and sine signal 603 is applied as input to dual channel, lock-in amplifier 605 as a Y-reference signal. For sake of understanding this embodiment, assume that conditioned reflectometer output signal 607 has a time dependence that is given by $\cos(\omega t-\phi)$, where φ is a phase related to a displacement direction by a dithering circle from a reference feature as disclosed in the '941 patent. As shown in FIG. 2, conditioned reflectometer output signal 607 is applied as input to dual channel, lock-in amplifier 605. In response, dual channel, lock-in amplifier 605 generates: (a) X position error signal 614 that is proportional to $\cos(\phi)$; and (b) generates Y position error signal 615 that is proportional to $\sin(s)$. In essence, dual channel, lock-in amplifier 605 determines the phase variation between: (a) the X-reference signal ($\cos(\omega t)$) and the Y-reference signal ($\sin(\omega t)$) that drive dither scanner 812; and (b) the conditioned reflectometer signal that is proportional to $\cos(\omega t-\phi)$. It does this by expanding terms of the type $\cos(\omega t)\cos(\omega t-\phi)$ and $\sin(\omega t)\cos(\omega t-\phi)$, integrating over a predetermined time period (to emulate the effect of integrating from $-\infty$ to $+\infty$), and low pass filtering the result to determine the X position error signal (proportional to $\cos(\phi)$ and the Y position error signal (proportional to $\sin(\phi)$ as DC offsets. It should be clear to those of ordinary skill in the art that embodiments of the present invention are not limited to the use of a dual channel, lock-in amplifier. In fact, further embodiments exist wherein the above-described operations may be carried out using, for example, a computer such as a personal computer.

As further shown in FIG. 2: (a) X position error signal 614, cosine signal 601, and DC offset signal 609 are applied as input to PID gain amplifier and summation circuit 608; and (b) Y position error signal 615, sine signal 603, and DC offset signal 610 are applied as input to PID gain amplifier and summation circuit 611. DC offset signals 609 and 610 may be used, for example, and without limitation, to: (a) calibrate embodiment 100; (b) set up initial X and Y offset positions for the tracking beam with respect to the scanning beam; and (c) reset embodiment 100 to adjust for drifts over time due to temperature variation, or other reasons. DC offset signals 609 and 610 are generated by DC offset modules 617 and 618, respectively, in accordance with any one of a number of methods that are well known to those of ordinary skill in the art (for example, using conventional electronics or a computer such as, for example, a personal computer), and DC offset signals 609 and 610 may be varied in response to user input in accordance with any one of a number of methods that are well known to those of ordinary skill in the art. It should also be understood that appropriate scale factors may be applied to X position error signal 614 and Y position error signal 615, respectively, which scale factors may be determined by calibrating embodiment 100 to ensure that the tracking beam follows the reference tracking feature.

As is well known, PID gain amplifier summation circuits 608 and 611, in response to predetermined parameters, add their three inputs and generate signals 612 and 613, respectively, as output. The predetermined parameters: (a) enable PID gain amplifier summation circuits 608 and 611 to integrate the respective error signals over a predetermined length of time to identify and ignore short-lived changes, and thereby, prevent jitter from affecting the system; and (b) enable PID gain amplifier summation circuits 608 and 611 to take the derivative of the respective error signals so that the respective error signals can be ignored when their rate of change is larger than a predetermined amount, and thereby, prevent jitter from affecting the system.

Signals 612 and 613 output from PID gain amplifier summation circuits 608 and 611, respectively, are applied as input to dither scanner 812. Thus, in accordance with one embodiment of the present invention, signal 612 is applied as input to a galvanometer that drives the X-direction dithering mirror of the pair of mirrors 316 and 317, and signal 613 is applied as input to a galvanometer that drives the Y-direction dithering mirror of the pair of mirrors 316 and 317. In response, the X-direction dithering mirror dithers the tracking beam along the X direction, and causes the tracking beam to follow the motion of the eye along the X direction. In addition, the Y-direction dithering mirror dithers the tracking beam along the Y direction, and causes the tracking beam to follow the motion of the eye along the Y direction.

Figure 3:
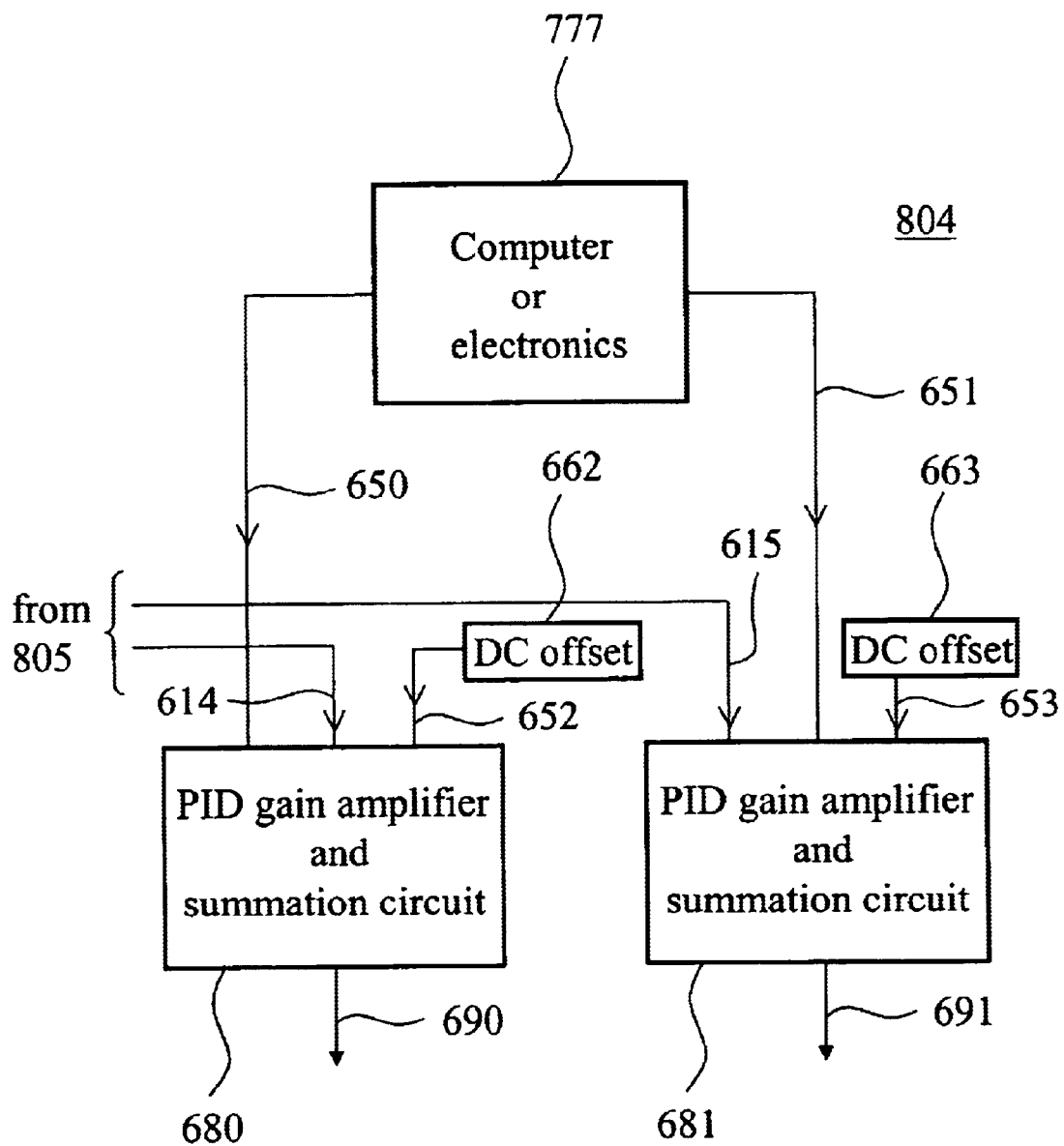
FIG. 3 is a functional block diagram of control module 804 that is fabricated in accordance with one embodiment of the present invention for use in the embodiment shown in FIG. 1.

FIG. 3 is a functional block diagram of control module 804 that is fabricated in accordance with one embodiment of the present invention for use in the embodiment shown in FIG. 1. As shown in FIG. 3, computer 777 (or conventional electronics circuit 777) generates OCT X scan signal 650 and OCT Y scan signal 651 (OCT X scan signals 650 and 651 are signals whose form depends on particular algorithms used to produce appropriate OCT scanning in the X and Y directions, respectively; and many methods are well known to those of ordinary skill in the art for generating such signals). As further shown in FIG. 3: (a) X position error signal 614 (generated in control module 805), OCT X scan signal 650, and DC offset signal 652 are applied as input to PID gain amplifier and summation circuit 680; and (b) Y position error signal 615 (generated in control module 805), OCT Y scan signal 651, and DC offset signal 653 are applied as input to PID gain amplifier and summation circuit 681. DC offset signals 652 and 653 may be used, for example, and without limitation, to: (a) calibrate embodiment 100; (b) set up initial X and Y offset positions for the tracking beam with respect to the scanning beam; and (c) reset embodiment 100 to adjust for drifts over time due to temperature variation, or other reasons. DC offset signals 652 and 653 are generated by DC offset modules 662 and 6663, respectively, in accordance with any one of a number of methods that are well known to those of ordinary skill in the art (for example, using conventional electronics or a computer such as, for example, a personal computer), and DC offset signals 652 and 653 may be varied in response to user input in accordance with any one of a number of methods that are well known to those of ordinary skill in the art. It should also be understood that appropriate scale factors may be applied to X position error signals 614 and 615, respectively, which scale factors may be determined by calibrating embodiment 100 to ensure that the tracking beam follows the reference tracking feature.

As is well known, PID gain amplifier summation circuits 680 and 681, in response to predetermined parameters, add their three inputs and generate signals 690 and 691, respectively, as output. The predetermined parameters: (a) enable PID gain amplifier summation circuits 680 and 681 to integrate the respective error signals over a predetermined length of time to identify and ignore short-lived changes, and thereby, prevent jitter from affecting the system; and (b) enable PID gain amplifier summation circuits 680 and 681 to take the derivative of the respective error signals so that the respective error signals can be ignored when their rate of change is larger than a predetermined amount, and thereby, prevent jitter from affecting the system.

Signals 690 and 691 output from PID gain amplifier summation circuits 680 and 681, respectively, are applied as input to scanner driver 803. Thus, in accordance with one embodiment of the present invention, signal 690 is applied as input to a galvanometer that drives the X-direction scanning mirror of the pair of mirrors 212 and 213, and signal 691 is applied as input to a galvanometer that drives the Y-direction scanning mirror of the pair of mirrors 212 and 213. In response, the X-direction scanning mirror scans the scanning beam along the X direction, and causes the scanning beam to follow the motion of the eye along the X direction. In addition, the Y-direction scanning mirror scans the scanning beam along the Y direction, and causes the scanning beam to follow the motion of the eye along the Y direction.

It should be clear to those of ordinary skill in the art that embodiments of the present invention are not limited to the use of a PID gain amplifier and summation circuit. In fact, further embodiments exist wherein the above-described operations carried out by the PID gain amplifier and summation circuit may be carried out using, for example, a computer such as a personal computer.

It should be understood that embodiments of the present invention are not limited to an apparatus wherein the scanning and tracking motion of the scanning beam, and the dithering and tracking motion of the tracking beam are produced by driving a scanning mechanism in the scanning arm and by driving a dither mechanism in the tracking arm. In fact, further embodiments exist wherein the tracking motion of the scanning beam and/or the tracking beam may be carried out by a separate tracking mechanism disposed in the scanning arm and/or the tracking arm, respectively. In accordance with such embodiments, the tracking signals would be distributed to the specific tracking mechanism(s) in a manner that should be clear to those of ordinary skill in the art in light of the discussion set forth above. Such tracking mechanisms could include paired reflectors of the type used to fabricate scanning mechanism 227 or dithering mechanism 329. Lastly, in accordance with such embodiments, dither mechanism 329 may be embodied, for example, utilizing resonant scanners or utilizing an embodiment disclosed in FIG. 3; of U.S. Pat. No. 6,325,512.

Those skilled in the art will recognize that the foregoing description has been presented for the sake of illustration and description only. As such, it is not intended to be exhaustive or to limit the invention to the precise form disclosed. For example, although embodiments of the present invention were described in relation to obtaining OCT scan images of an eye, the present invention is not limited thereby, In particular, it is within the scope and spirit of the present invention to encompass method and apparatus for obtaining OCT images of any type of material such as, for example and without limitation, animal, human, and plant tissue. Advantageously, use of one or more embodiments of the present invention can utilize axial scan rates below about 500 Hz, including axial scan rates in a range from about 150 Hz to about 350 Hz.

What is claimed is:

1. An optical coherence tomography ("OCT") application apparatus which performs an OCT application on an object, which OCT application apparatus comprises:
   an OCT scanning apparatus which outputs a scanning beam of OCT scanning radiation; and
   an active tracking system that generates and projects a tracking beam of tracking radiation onto a region including a reference tracking feature;
   wherein the active tracking system further comprises an analysis system that analyzes tracking radiation reflected from the region to detect movement of the object and to generate tracking signals, and applies the tracking signals: (a) to direct the active tracking system to move the tracking beam to follow the movement of the object, and (b) as input to the OCT scanning apparatus, to direct the OCT scanning apparatus to move the scanning beam to follow the movement of the object.

2. The OCT application apparatus of claim 1 wherein the active tracking system comprises a dither mechanism that moves the tracking beam.

3. The OCT application apparatus of claim 1 wherein: (a) the active tracking system further comprises a photodetector which produces a signal in response to the reflected tracking radiation; and (b) analysis system analyzes changes in the signal output from the photodetector caused, in turn, by changes in intensity of the reflected tracking radiation due to reflectance differences in the region between the reference tracking feature and its surrounding or adjacent area.

4. The OCT application apparatus of claim 3 wherein dither signals applied to the dither mechanism cause the tracking beam to move in an oscillatory pattern.

5. The OCT application apparatus of claim 4 wherein the analysis system comprises a detection module that determines phase variations between the dither signals and the signal output from the photodetector.

6. The OCT application apparatus of claim 5 wherein the detection module, in response to the phase variations, determines the tracking signals.

7. The OCT application apparatus of claim 6 wherein:
   the OCT scanning apparatus comprises an OCT scanning mechanism, which OCT scanning mechanism is driven by OCT sum signals comprised of sums of OCT scanning signals that produce a predetermined scan pattern on the object in a direction perpendicular to an axial scan direction, and the tracking signals; and
   the dither mechanism is driven by dither sum signals comprised of sums of the dither signals, and the tracking signals.

8. The OCT application of claim 7 wherein:
   the tracking signals comprise a first direction control signal and a second direction control signal.

9. The OCT application of claim 8 wherein:
   the OCT scanning mechanism comprises a first and a second scanner driver coupled to a pair of orthogonally mounted reflectors; and
   the dither mechanism comprises a first and a second dither driver coupled to a pair of orthogonally mounted reflectors.

10. The OCT application apparatus of claim 9 wherein the dither mechanism causes the beam of tracking radiation to move in an oscillatory motion in the first direction and in the second direction, the oscillatory motion in the first direction and the second direction having a first phase and a second phase, respectively.

11. The OCT application apparatus of claim 10 wherein the first and second phases of oscillatory motion are orthogonal to each other, and the oscillatory motion in the first and second directions have substantially identical amplitudes.

12. The OCT application apparatus of claim 8 wherein the detection module comprises lock-amplifiers that determine error signals proportional to phase variations in response to the dither signals and the signals output from the photodetector and PID gain amplifier and summation circuits that determine the tracking signals in response to the dither signals and the error signals.

13. The OCT application apparatus of claim 1 which further comprises a fundus illumination apparatus and a viewing apparatus.

14. The OCT application apparatus of claim 1 wherein the OCT scanning apparatus which outputs a beam of OCT scanning radiation causes the OCT scanning radiation to scan relatively slowly, whereby a signal-to-noise ratio of images generated by performing such a slow scan is higher that that obtained using a relatively rapid scan.

15. The OCT application apparatus of claim 1 which further comprises an analyzer that receives OCT scanning radiation reflected from the object from the OCT scanning apparatus, which analyzer produces one or more of an image, measurements of retinal and retinal nerve fiber layer thickness, and mapping a topography of an optic nerve head.

16. The OCT application apparatus of claim 1 wherein the object is an eye and the reference tracking feature is one of: a reference tracking feature associated with the eye and a retro-reflecting material.

17. The OCT application apparatus of claim 16 wherein the reference tracking feature associated with the eye is one of: an intersection of two blood vessels and an optical nerve head.

18. An OCT application method which comprises steps of:

outputting a scanning beam of OCT scanning radiation; and generating and projecting a tracking beam of tracking radiation onto a region including a reference tracking feature; and detecting and analyzing tracking radiation reflected from the region to detect movement of the object and to generate tracking signals;

wherein the step of outputting includes utilizing the tracking signals to cause the scanning beam to follow movement of the object; and wherein the step of projecting includes utilizing the tracking signals to cause the tracking beam to follow movement of the object.

19. The OCT application method of claim 18 wherein the step of projecting includes dithering.

20. The OCT application method of claim 19 wherein the step of analyzing includes determining phase variations between signals producing the dithering and a signal produced by the reflected tracking radiation.

* * * * *